United States Patent [19]
Asp et al.

[11] Patent Number: 5,759,784
[45] Date of Patent: Jun. 2, 1998

[54] METHOD OF NUCLEIC ACID TRANSFER

[75] Inventors: Allan Asp, Uppsala; Peder Carstenius, Bagarmossen; Ulf Landegren, Uppsala, all of Sweden

[73] Assignee: Pharmacia Biotech AB, Uppsala, Sweden

[21] Appl. No.: 737,006

[22] PCT Filed: May 5, 1995

[86] PCT No.: PCT/SE95/00492

§ 371 Date: Oct. 31, 1996

§ 102(e) Date: Oct. 31, 1996

[87] PCT Pub. No.: WO95/30773

PCT Pub. Date: Nov. 16, 1995

[30] Foreign Application Priority Data

May 6, 1994 [SE] Sweden ............... 9401594-8

[51] Int. Cl.⁶ ............. C12Q 1/68; C12P 19/34; G01N 33/553
[52] U.S. Cl. ............. 435/6; 435/91.2; 435/287.1; 435/287.2; 436/174; 514/44
[58] Field of Search ............. 435/6, 91.2, 287.1, 435/287.2; 514/44; 436/174

[56] References Cited

U.S. PATENT DOCUMENTS 4,882,127  11/1989  Rosenthal et al. ............. 422/50
5,512,439  4/1996   Hornes et al. ............. 435/6

FOREIGN PATENT DOCUMENTS

279506 A1   6/1990  Germany.
93-15228    8/1993  WIPO.
WO94/11421  5/1994  WIPO.
WO94/11529  5/1994  WIPO.

Primary Examiner—Stephanie W. Zitomer
Assistant Examiner—Paul B. Tran
Attorney, Agent, or Firm—Birch, Stewart, Kolasch and Birch, LLP

[57] ABSTRACT

The present invention is drawn to a method of dosaging a nucleic acid species comprising contacting a solid phase member or members, each member having a predetermined capacity of binding said nucleic acid species, with a sample containing the nucleic acid species to bind the nucleic acid species thereto, and then releasing the bound nucleic acid species into a desired processing or analytical means.

14 Claims, 3 Drawing Sheets

METHOD OF NUCLEIC ACID TRANSFER

This application is a 371 filing, the National Stage of PCT/SE95/00492, filed May 5, 1995.

TECHNICAL AREA OF THE INVENTION

The present invention relates to the dosaging of nucleic acid fragments, and more particularly to the transfer of a predetermined amount of a nucleic acid species from a sample solution to a processing or analytical means.

BACKGROUND OF THE INVENTION

The vast majority of DNA in higher organisms is identical in sequence among the chromosomes of different individuals. A small fraction of DNA, however, is variable or polymorphic in sequence among individuals, the formal definition of polymorphism being that the most frequent variant (or allele) has a population frequency which does not exceed 99%.

The analysis of DNA polymorphisms was originally based on the variations in the lengths of DNA fragments produced by restriction enzyme digestion due to sequence variations in one of the recognition sites for the specific enzyme used, hence the name restriction fragment length polymorphisms (RFLP's). The DNA fragment lengths are determined based on their migration rates on an electrophoretic gel, and a specific set of fragments may be characterized by its fragment pattern. Visualization of the separated fragment bands may be performed by blotting techniques using e.g. radioactively labelled probes.

The DNA fragments to be analysed may also be produced by amplification of polymorphic loci, such as by PCR (polymerase chain reaction) with suitable primers. This technique is particularly applicable to the analysis of polymorphic markers represented by repeated sequence motifs, such as di-, tri- or tetranucleotide repeats. Such variations may also be implicated in human disease, as exemplified by the fragile X syndrome and Huntington's disease caused by trinucleotide repeats. In the case of amplified fragments, detection of the fragments may easily be provided for by labelling the primer/primers, or one or more of the nucleotides used in the extension reactions, with a fluorophore, e.g. fluorescein. For instance, for use of fragment analysis in forensic medicine, a set of, say, four different primer pairs may be selected which together give a fragment analysis pattern with a 99.9% security in distinguishing between individuals. The primers are designed to generate products with a moderate variation, which taken together give such a high security. Today, the fragment analysis are often performed in automatic DNA sequencing apparatus using fluorescent label detection. A problem when analysing fragments produced by amplification procedures, such as PCR, or RFLP (restriction fragment length polymorphism) on DNA sequencing apparatus is to load the correct amount of amplified product on the electrophoretic gel. While a PCR reaction normally generates DNA product quantities of the order of picomoles, only a quantity of the order of attomole to femtomole, i.e. a factor of 1000 less or more, is required for fragment analysis. Many times the signals tend to "hit the ceiling" due to overloading of the fragment product. Of course, the amount of PCR products also vary considerably with the degree of success of the amplification. It is therefore common practice to dilute the samples prior to making a test loading on the gel, or to produce a serial dilution series to ensure that a correct sample concentration is obtained for some dilution.

SUMMARY OF THE INVENTION

The object of the invention is to provide a method for accurate dosaging of nucleic acid species from a sample solution to a processing or analytical unit, such as a reaction vessel or an electrophoretic gel or capillary. In particular, the invention seeks to overcome the above discussed problem in fragment analysis.

WO 94/11529 discloses the use of a manifold with multiple solid phase members, such as a comb structure, for the capturing and transfer of nucleic acid species from a receptacle or receptacles to an analyzer unit where the nucleic acid species is released. The present invention proposes a development and generalization of that concept to the extent that it be applied to the dosaging of a predetermined amount of nucleic acid from a sample solution into a processing or analytical unit. This is accomplished by properly adjusting the binding capacity of each solid phase member with respect to the nucleic acid species so that a predetermined quantity of the nucleic acid species will bind to the solid phase members and a controlled amount will then be released into the desired processing or analytical unit.

Thus, the invention generally provides a method for dosaging a nucleic acid species, which method comprises contacting a solid phase member or members, each member having a predetermined capacity of binding said nucleic acid species, with a sample containing the nucleic acid species to bind the nucleic acid species thereto, and then releasing the bound nucleic acid species into a desired processing or analytical means. With the present invention it is possible to dosage a predetermined amount of nucleic acid species, from a high concentrated solution as well as from a solution with a low concentration. In a preferred embodiment the amount of nucleic acid species in the sample is in an amount exceeding the capacity of the solid phase member or members. It is also possible, with the method according to the invention, to concentrate a sample with a low amount of nucleic acid species, an amount below the binding capacity of the solid phase member. The low concentration can be the result of bad amplification. By contacting the solid phase member with the bad amplified sample the predetermined amount will bind to the member.

While the invention thus generally relates to accurate dosaging of nucleic acid species, usually DNA, in a preferred embodiment of the invention the nucleic acid species are fragments generated by amplification reactions, such as PCR, which fragments are loaded on an electrophoretic gel or capillary in a fragment analysis procedure.

The term solid phase members is to be understood in a broad sense and includes e.g. beads, such as magnetic beads, dip-sticks, etc. Preferably, however, the solid phase members are part of a manifold of the type disclosed in the aforementioned WO 94/11529, as will be described below.

DETAILED DESCRIPTION OF THE INVENTION

Figure 1:
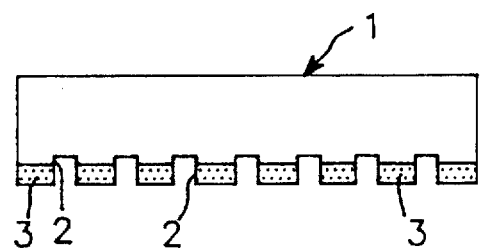
FIG. 1 is a front view of a comb-like manifold with eight prongs.

The comb-like manifold schematically illustrated in FIG. 1 and generally designated by reference numeral 1 is disclosed in WO 94/11529 (the disclosure of which is incorporated by reference herein). The manifold 1 has eight prongs or teeth 2. The shape of the teeth 2 and their spacing are adapted to the sample wells of an electrophoretic apparatus as will be described in more detail below. In the figure, the teeth 2 have been derivatized, indicated by shading 3, e.g. coated with avidin-conjugated particles as described in Example 1 below.

Figure 2:
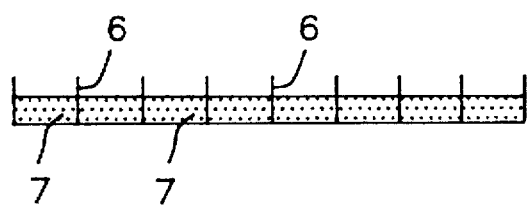
FIG. 2 is a schematic sectional view of a well strip with eight wells.

The manifold 1 is designed to cooperate with corresponding well set, such as that shown in FIG. 2, which has eight individual wells 6, each well 6 being adapted to receive a single manifold tooth 2 and here also shown as partially filled with sample solution 7.

Figure 3:
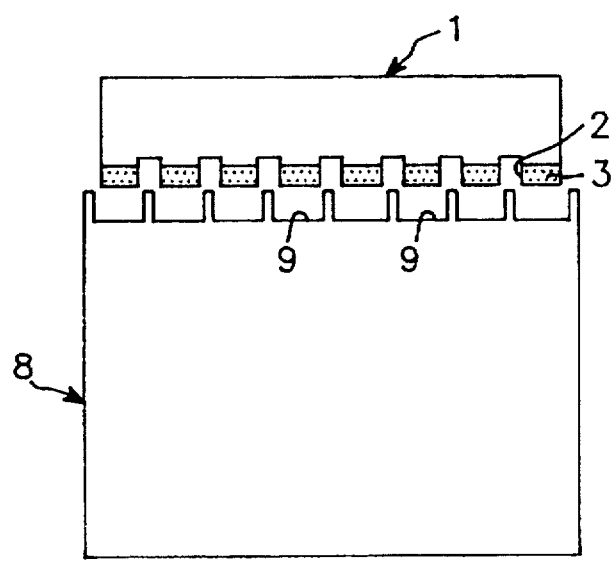
FIG. 3 is a schematic front view showing the manifold of FIG. 1 aligned with the sample wells of an analytical apparatus.

As mentioned above, manifold 1 is adapted to cooperate with the sample wells of an analytical apparatus. This is schematically illustrated in FIG. 3, where manifold 1 is placed above an electrophoretic apparatus, generally designated by reference numeral 8, with the teeth 2 aligned with and capable of being received in respective sample wells 9 of the electrophoretic apparatus.

To permit the binding of said nucleic acid species to the comb teeth 2, there is immobilized to each tooth surface a molecule or group capable of interacting (i) with the nucleic acid species per se or (ii) with a functional group or molecule incorporated into the nucleic acid species.

In the first case (i), the solid phase, surface may support an oligonucleotide, e.g. covalently bound to the solid phase, which oligonucleotide is complementary with and therefore capable of hybridizing with the nucleic acid species. In case the nucleic acid species is an amplification product, such as obtained by PCR, the hybridizing region thereof should be located internally to prevent the oligonucleotide from hybridizing with non-extended primers in the reaction solution.

In the second case (ii), the functional group incorporated into the nucleic acid may be one member of a specific binding pair, the other member being supported by the solid phase. Exemplary of such binding pairs are biotin - avidin, biotin - streptavidin, cystein - thiol groups, antigen antibody, lectin - sugar. A particularly useful binding pair in the present context is biotin - avidin (or streptavidin). The use of such a specific binding pair for immobilizing DNA to a solid phase is described in more detail in e.g. WO 89/099282 (the disclosure of which is incorporated by reference herein).

An alternative binding principle (iii) which is advantageous in the context of amplification products is the use of a DNA binding protein on the comb teeth surfaces, which protein recognizes sequences added to the 5'-end of an amplification primer, which sequences, however, only can be bound in double stranded form, as is per se known in the art. Such an approach would also prevent the capturing of primers by the solid phase.

For the purposes of the invention, the comb teeth 2 may advantageously be provided with a substantially expanded surface area, permitting increased surface loading, by coating the surfaces with porous particles. A suitable coating method involving the attachment of particles to the surface without the use of adhesive is described in WO 94/11421 (the disclosure of which is incorporated by reference herein).

Such particle coating of the solid phase members will readily provide for the achievement of sufficient binding capacities for the intended purposes.

The immobilization to the solid phase surface of predetermined quantities of the group or molecule capable of binding the nucleic acid species such that a well defined binding capacity is obtained is readily performed by the skilled person with guidance of the above and well known methods in the art.

By introducing the comb teeth 2 into a solution containing the desired nucleic acid species, an amount thereof determined by the binding capacity of the prepared teeth is bound to each tooth surface. This bound nucleic acid material may then be transferred to and released in a desired processing or analytical unit. The necessary environment and conditions for the release or description of the nucleic acid material from the comb teeth varies depending on the particular species to be released and the particular processing or analytical unit. For example, in the case of an analysis comprising gel electrophoresis, the manifold is designed such that the solid phase members thereof may be conveniently introduced into the sample wells of the electrophoretic gel plate, in which wells desorption of the synthesized nucleic acid strands may be effected by means of, for example, a denaturant, such as formamide, heat and/or a denaturing pH, e.g. alkali.

An exemplary use of the comb structure in FIG. 1 in fragment analysis will now be described.

First, a PCR amplification is performed on chromosomal DNA, utilizing a battery of primer pairs selected to provide for the amplification of specific loci exhibiting some type of polymorphism. One primer in each pair is labelled with a detectable element, such as a fluorophore, say, e.g., fluorescein, and the other primer in the primer-pair is labelled with a separation element, such as one member of a specific binding pair, say, e.g., biotin. When the PCR amplification is completed, the reaction solution contains inter alia double stranded amplification products, wherein one strand carries fluorescein and the other strand has a biotin end, as well as non-extended primers. In the illustrated case, eight different PCR amplifications may be performed in the eight wells 6 of the receptacle in FIG. 2.

Prior to the PCR amplification, the teeth 2 of a comb 1 in FIG. 1 have been provided with a predetermined amount of avidin, for example by the above described coating procedure. This amount has been selected to provide a defined biotin binding capacity of the teeth 2 which is well below the expected level of biotin-labelled PCR products in the reaction solution. The comb teeth 2 are then inserted into the corresponding wells 6 to capture the desired quantity of biotin-labelled double stranded amplified DNA products corresponding to the polymorphic loci of the chromosomal DNA.

After washing of the comb teeth 2 with bound DNA fragments, the comb 1 is now transferred to and aligned with the electrophoretic apparatus 8 as shown in FIG. 3, and the manifold teeth 2 are introduced into the sample wells 9 of the electrophoretic apparatus 8. This apparatus may, for instance, be an automatic DNA sequencer, for example an A.L.F. Sequencer™ (supplied by Pharmacia LKB Biotechnology AB, Sweden) which has 40 electrophoresis lanes, laser light excitation and photodiode detectors or detection of fluorescence, one detector for each lane. The fluoresceinlabelled strands of each bound DNA fragment are then melted off, e.g. by the sample wells 8 containing a suitable agent solution, e.g. formamide, for effecting elution of the strands. After elution for a few minutes, the comb 1 is lifted out from the wells 9, and the electrophoretic process is started. Hereby a predetermined well defined amount of labelled DNA fragments have been applied to the electrophoretic gel, insuring that an appropriate signal within the dynamic range of the analyzer is obtained. From the migration patterns obtained in each lane, polymorphic characteristics are determined in conventional manner.

Experiments have indicated that the binding of double stranded PCR products are not affected to any great extent by even a large excess of biotinylated primers, as shown in Example 2 below.

In the following, the preparation of a multipronged manifold with coated prongs as well as binding tests with a biotin-coated manifold are illustrated by two non-limiting examples.

EXAMPLE 1

A. Conjuration of avidin to sepharose® particles

Sepharose® particles (HiTrap®, NHS-activated Sepharose® HP, Pharmacia LKB Biotechnology AB, Uppsala Sweden) corresponding to 6.0 ml of sedimented material, were carefully washed with ice cold 1 mM HCl (3×10 ml) on a sintered funnel, making sure that the Sepharose® surface did not at any time become dry. The particles were quickly washed with a solution of 1.0 M NaCl and 0.4 M NaHCO$_3$, buffered to pH 8.3, and transferred to a final volume of 5 ml of the above buffer, containing 10 mg of avidin. The suspension was incubated rotating end-over-end for one hour, filtered, and the particles were blocked in 0.1 M ethanolamine buffer, pH 8.3, for 15 minutes. The avidin-conjugated Sepharose® particles were then washed with 0.1 M acetate buffer, pH 4.0, and used immmediately or stored in 0.05 M Tris-buffer, pH 7.3, with 0.02% (w/v) sodium azide.

B. Attachment of particles to a polystyrene solid support

Avidin-conjugated particles as prepared above were filtered, washed with distilled water, dried with methanol (3×5 ml), and then equilibrated with triethylamine (Et$_3$N; 3×5 ml). The solid was quickly transferred to a suitable vessel and Et$_3$N was added to obtain a slurry of about 75% (v/v) particles. A polystyrene support, configured as a microtiter plate lid with 8 rows of 12 pin-and-ball extensions adapted to project into individual microtiter wells of a corresponding microtiter plate (F.A.S.T. system, Falcon, Oxnard, Calif., U.S.A.) was washed with ethanol for 20 minutes in an ultrasonic bath and the particles were then grafted onto the projections from the polystyrene support by two submersions in the slurry, each for 2 seconds, followed by immediate evaporation of the residual Et$_3$N in air. After washing in deionized water, detached particles were collected and reused. Loosely bound particles were removed by a 10 minutes incubation shaking in water. The manifold was stored until use in buffer (1 M NaCl, 100 mM Tris-HCl, pH 7.5, and 0.1 (v/v) Triton X 100), with the addition of 0.5% (w/v) fat-free dry milk and 0.02% sodium azide.

Testing of the binding capacity of the avidin-coated support by means of a $^{32}$P-labelled oligonucleotide, 5'-modified with biotin, indicated that each prong of the support could bind in the order of 20 pmol of biotinylated oligonucleotides.

By the guidance of the above, the person skilled in the art may readily prepare solid phase surfaces of any desired type with a desired binding capacity for each special application.

EXAMPLE 2

Study of the influence of residual primer concentration on the binding of PCR products 20 µl PCR amplification reactions were carried out on the DQB-gene in separate wells (DQB is a transplantation antigen) using biotinylated and radioactively labelled primers, respectively. After completed amplification, the PCR products were purified from the primers. Different amounts of biotinylated primer were then added to each well.

Figure 4:
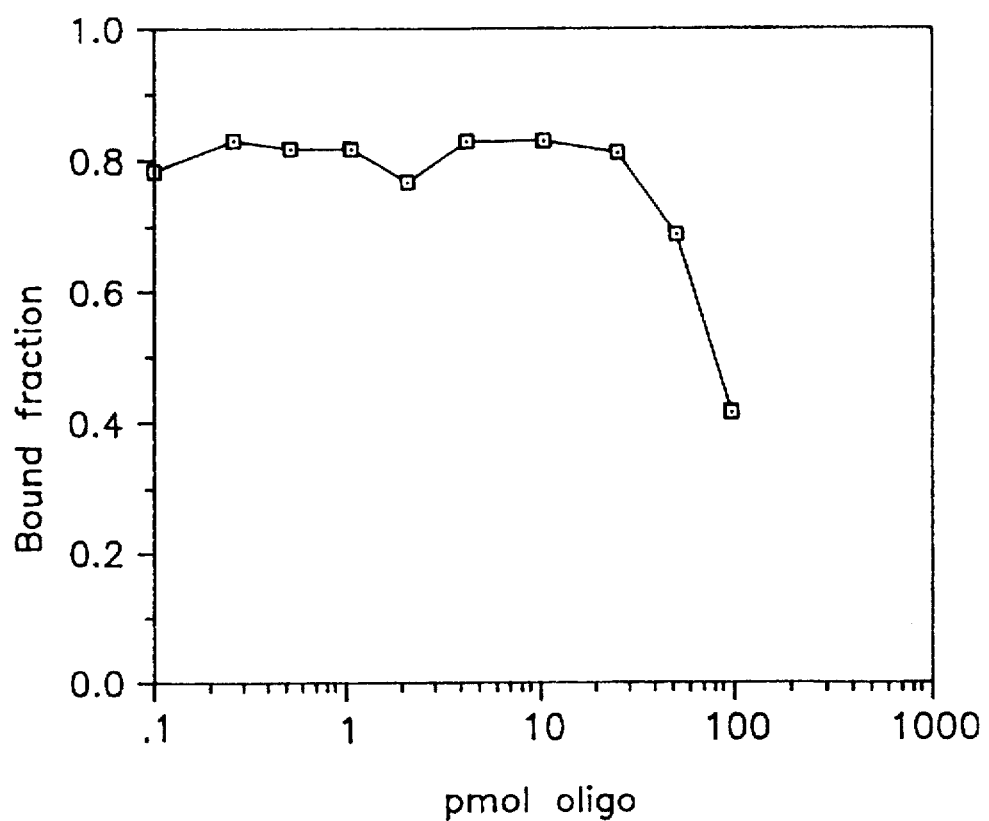
FIG. 4 is a diagram showing the binding of biotinylated PCR product to a streptavidin coated manifold of FIG. 1 in the presence of varying concentrations of biotinylated primer.

In successive experiments, the teeth of a polystyrene comb of the type shown in FIG. 1, the tips of which had been coated with streptavidin-Sepharose® by the procedure described in Example 1, were then inserted and incubated in each well to bind the amplified DQB-gene product thereto. The total radioactivity as well as the radioactivity of the comb after removal thereof from the well and washing were then measured. The results are shown in FIG. 4, where the fraction of bound PCR products is plotted against the concentration of biotinylated primer (pmol oligo).

As can be seen from the diagram, substantially the same fraction is bound independently of the concentration of biotinylated primers up to a high primer concentration.

EXAMPLE 3

Figure 5:
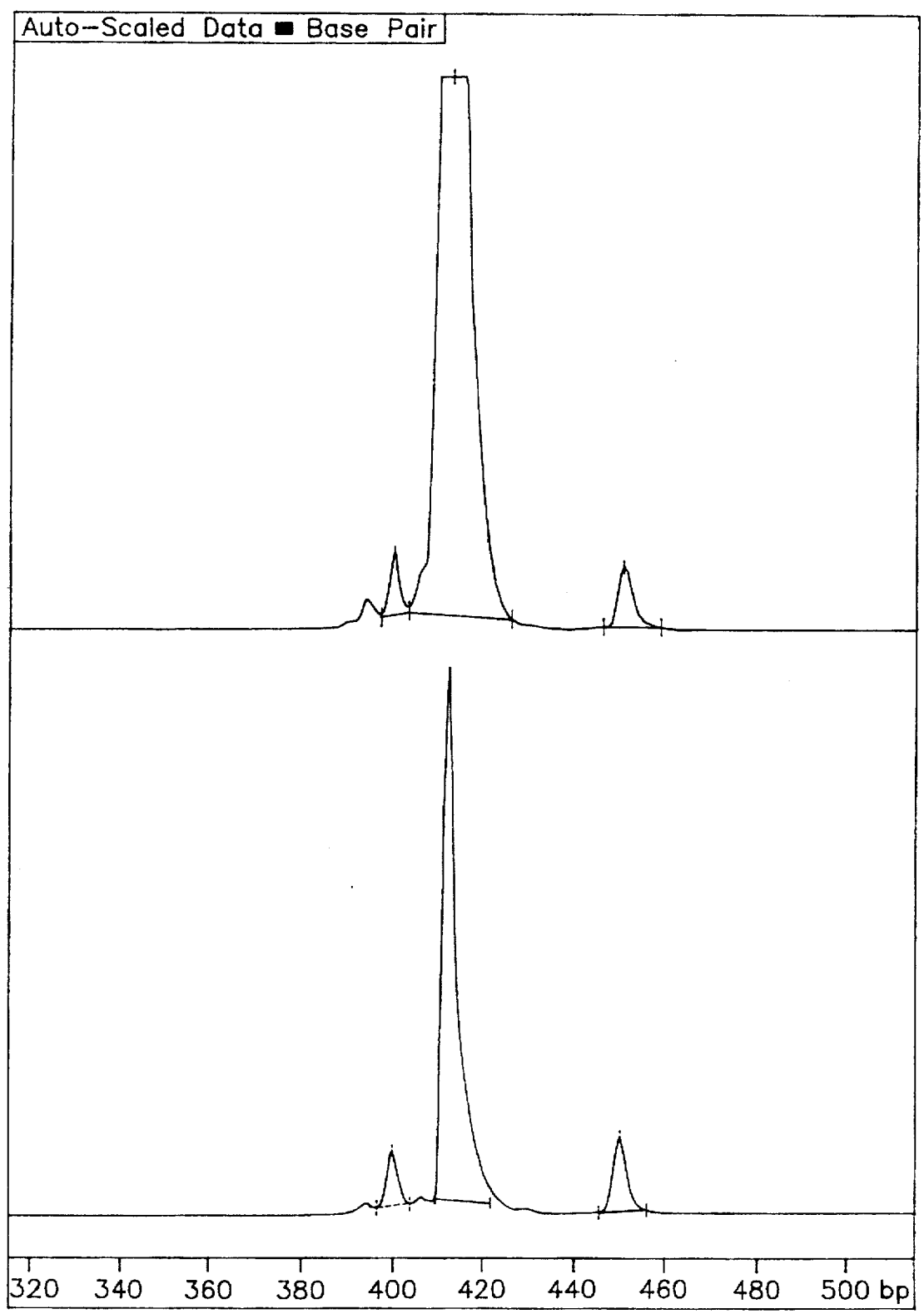
FIG. 5 present two chromatograms showing the problem with overloading of fragment product.

In a further experiment the teeth of a polystyrene comb of the type shown in FIG. 1, the tips of which had been coated with streptavidin-Sepharose by the procedure described in Example 1, were inserted and incubated in each well to bind the amplified product thereto. The result is shown in FIG. 5. In the chromatograms in FIG. 5 the main peaks refer to samples and the small peaks to internal references. In the first chromatogram 1 µl of the original sample has been loaded directly onto the instrument. As can be seen from the figure the main peak has "hit the ceiling" due to saturation of the detector. In the second chromatogram the solid phase member, with a predetermined binding capacity, has been contacted with the original sample for 5 minutes, whereafter the solid phase member has been placed on the instrument, whereby the sample is eluated and detected. The obtained sample peak is within the upper limit of the instrument.

The invention is, of course, not-restricted to the embodiments specifically described above and shown in the drawings, but many changes and modifications may be made without departing from the scope of the general inventive concept as defined in the following claims.

We claim:

1. A method of dosaging a nucleic acid species, comprising
   (i) contacting a solid phase member or members, each member having a predetermined capacity of binding said nucleic acid species, with a sample containing the nucleic acid species to bind said nucleic acid species thereto; and
   (ii) releasing the bound nucleic acid species into a means of processing or analyzing said nucleic acid.

2. A method of claim 1, wherein the amount of nucleic acid species in the sample is in an amount exceeding the binding capacity of the solid phase member or members.

3. A method of claim 1, wherein the amount of nucleic acid species in the sample is in an amount below the binding capacity of the solid phase member or members.

4. The method of claim 1, 2 or 3, wherein said nucleic acid species are products obtained in amplification reactions.

5. The method of claim 1 further comprising
   a) binding double stranded DNA via one strand thereof to the solid phase member or members; and
   b) releasing the other DNA strand to said processing or analytical means.

6. The method of claim 1, wherein said release of the nucleic acid species from the solid phase is effected by treatment with a denaturant.

7. The method of claim 6, wherein the denaturant is selected from the group consisting of formamide, heat with a denaturing pH, and a combination thereof.

8. The method of claim 7 wherein the denaturing pH is alkali.

9. The method of claim 1, wherein said solid phase members are part of a manifold.

10. The method of claim 5 wherein the manifold is a comb-like element having teeth which form said solid phase members.

11. The method of claim 12, wherein said analytical means comprises an electrophoretic separation gel or capillary and has sample wells adapted to receive said manifold teeth.

12. The method of claim 10 wherein said comb-like element has four teeth.

13. The method of claim 10 wherein said comb-like element has eight teeth.

14. A method of nucleic acid fragment analysis comprising
   (i) creating one or more nucleic fragment species;
   (ii) dosaging the nucleic acid fragment species according to the method of claim 1; and
   (iii) analyzing said nucleic acid fragment species.

* * * * *